US008396187B2

(12) United States Patent
Safai (10) Patent No.: US 8,396,187 B2
(45) Date of Patent: Mar. 12, 2013

(54) X-RAY INSPECTION TOOL

(75) Inventor: Morteza Safai, Seattle, WA (US)

(73) Assignee: The Boeing Company, Chicago, IL (US)

( * ) Notice: Subject to any disclaimer, the term of this patent is extended or adjusted under 35 U.S.C. 154(b) by 308 days.

(21) Appl. No.: 12/965,159

(22) Filed: Dec. 10, 2010

(65) Prior Publication Data

US 2012/0148026 A1     Jun. 14, 2012

(51) Int. Cl.
*G01B 15/06*     (2006.01)
(52) U.S. Cl. .............................. 378/58; 378/87; 378/197
(58) Field of Classification Search .................... 378/57, 378/58, 70, 86–90, 193, 197
See application file for complete search history.

(56) References Cited

U.S. PATENT DOCUMENTS

| | | | |
|---|---|---|---|
| 5,411,890 A | 5/1995 | Falat | |
| 5,429,009 A | 7/1995 | Wolfe et al. | |
| 5,466,605 A | 11/1995 | Glaunsinger et al. | |
| 5,482,890 A | 1/1996 | Liu et al. | |
| 6,379,622 B1 | 4/2002 | Polak et al. | |
| 6,564,620 B1 | 5/2003 | Jaeger | |
| 6,627,914 B1 | 9/2003 | Komiyama et al. | |
| 6,657,232 B2 | 12/2003 | Morkoc | |
| 6,710,366 B1 | 3/2004 | Lee et al. | |
| 6,717,664 B2 | 4/2004 | Floyd et al. | |
| 7,002,079 B2 | 2/2006 | Mitchell et al. | |
| 7,005,669 B1 | 2/2006 | Lee | |
| 7,026,641 B2 | 4/2006 | Mohseni et al. | |
| 7,212,283 B2 | 5/2007 | Hother et al. | |
| 7,253,004 B2 | 8/2007 | Vossmeyer et al. | |
| 7,304,305 B2 | 12/2007 | Hunt | |
| 7,306,823 B2 | 12/2007 | Sager et al. | |
| 7,342,235 B1 | 3/2008 | Harrison et al. | |
| 7,345,596 B2 | 3/2008 | Wallach et al. | |
| 7,513,941 B2 | 4/2009 | Frey et al. | |
| 7,528,372 B2 | 5/2009 | Garvey, III et al. | |
| 7,529,343 B2 | 5/2009 | Safai et al. | |
| 7,534,489 B2 | 5/2009 | Ying et al. | |
| 7,535,990 B2 | 5/2009 | Safai et al. | |

(Continued)

FOREIGN PATENT DOCUMENTS

| | | |
|---|---|---|
| EP | 1130385 | 9/2001 |
| EP | 1245949 | 10/2002 |

(Continued)

OTHER PUBLICATIONS

U.S. Appl. No. 12/952,652, filed Nov. 23, 2010, Safai.

(Continued)

*Primary Examiner* — Jurie Yun
(74) *Attorney, Agent, or Firm* — Yee & Associates, P.C.

(57) ABSTRACT

The different advantageous embodiments provide an apparatus and a method for inspecting a surface of a work piece. In one advantageous embodiment, an apparatus comprising a number of tracks, a support structure, connection system, and controller is disclosed. The number of tracks are configured for placement along a path. The support structure is configured to move on the number of tracks. The X-ray system is moveably connected to the support structure. The X-ray system is configured to send a plurality of X-rays toward a work piece and is configured to move along an axis through the support structure. The connection system is configured to removably connect the number of tracks to the work piece using a vacuum applied to a surface of the work piece. The controller is configured to activate and deactivate the X-ray system based on an amount of vacuum applied to the surface of the work piece.

20 Claims, 8 Drawing Sheets

U.S. PATENT DOCUMENTS

| | | |
|---|---|---|
| 7,567,649 B1 | 7/2009 | Safai et al. |
| 7,623,626 B2 | 11/2009 | Safai et al. |
| 7,649,967 B2 | 1/2010 | Jonsson |
| 7,649,976 B2 | 1/2010 | Georgeson et al. |
| 7,780,913 B2 | 8/2010 | Farmer |
| 7,785,717 B2 | 8/2010 | Barbera-Guillem |
| 7,807,265 B2 | 10/2010 | Santra et al. |
| 7,887,938 B2 | 2/2011 | Fristad et al. |
| 7,902,524 B2 | 3/2011 | Safai et al. |
| 7,925,452 B2 | 4/2011 | Safai et al. |
| 7,955,858 B2 | 6/2011 | Davis et al. |
| 7,976,726 B2 | 7/2011 | Wang et al. |
| 2003/0068824 A1 | 4/2003 | Frankel et al. |
| 2003/0109056 A1 | 6/2003 | Vossmeyer et al. |
| 2003/0160182 A1 | 8/2003 | Petrich et al. |
| 2004/0211894 A1 | 10/2004 | Hother et al. |
| 2005/0200481 A1 | 9/2005 | Wallach |
| 2006/0062902 A1 | 3/2006 | Sager et al. |
| 2006/0068203 A1 | 3/2006 | Ying et al. |
| 2006/0152706 A1 | 7/2006 | Butland |
| 2007/0042139 A1 | 2/2007 | Cooper et al. |
| 2007/0048867 A1 | 3/2007 | Farmer |
| 2007/0110960 A1 | 5/2007 | Frey et al. |
| 2007/0189454 A1 | 8/2007 | Georgeson et al. |
| 2007/0194297 A1 | 8/2007 | McCarthy et al. |
| 2007/0264719 A1 | 11/2007 | Santra et al. |
| 2010/0151577 A1 | 6/2010 | Davis et al. |
| 2010/0213387 A1 | 8/2010 | Safai et al. |
| 2011/0176962 A1 | 7/2011 | Davis et al. |

FOREIGN PATENT DOCUMENTS

| | | |
|---|---|---|
| WO | 9805946 | 2/1998 |
| WO | 0214785 | 2/2002 |
| WO | 2005124340 | 12/2005 |
| WO | 2006107331 | 10/2006 |
| WO | 2006107493 | 10/2006 |
| WO | 2007130545 | 11/2007 |
| WO | 2007130576 | 11/2007 |
| WO | 2009055284 | 4/2009 |
| WO | 2010077930 | 7/2010 |
| WO | 2012071118 | 5/2012 |

OTHER PUBLICATIONS

Dunn, "Flaw detection by X-ray scanning using the rolling-window template-matching procedure", Applied Radiation and Isotopes, Elsevier, vol. 61, Copyright 2004, pp. 1217-1225.

Dyba et al., "STED-Microscopy overcomes the diffraction limit in a fundamental way.", retrieved Jun. 15, 2012, 3 pages http://www3.mpibpc.mpg.de/groups/hell/STED.htm.

"Group (periodic table)", Wikipedia, retrieved Jun. 15, 2012, 3 pages http://en.wikipedia.org/wiki/Group_(periodic_table).

"Making Nanodots Useful for Chemistry", ScienceDaily, Jun. 19, 2003, retrieved Jun. 15, 2012, 2 pages http://www.sciencedaily.com/releases/2003/06/030619075658.htm.

"Single Photon Detection", Quantum Information Group, Toshiba Research Europe Ltd., Cambridge Research Laboratory, retrieved Jun. 15, 2012, 2 pages http://www.toshiba-europe.com/research/crl/qig/singlephotondetection.html.

Westphal et al., "Nanoscale Resolution in the Focal Plane of an Optical Microscope", Physical Review Letters, The American Physical Society, Apr. 2005, 4 pages.

"[3-(2-Aminoethyl)aminopropyl]trimethoxysilane", ScienceLab, retrieved Jun. 15, 2012, 2 pages http://www.sciencelab.com/page/S/PVAR/SLA3115.

PCT Search Report dated Mar. 31, 2010 regarding international application No. PCT/US2009/068223, applicant The Boeing Company, 5 pages.

PCT Search Report dated Jun. 1, 2012 regarding international application No. PCT/US2011/057030, applicant The Boeing Company, 4 pages.

PCT Search Report dated Jan. 19, 2012 regarding international application No. PCT/US2011/057892, applicant The Boeing Company, 5 pages.

USPTO Office Action dated Feb. 10, 2012 for U.S. Appl. No. 13/070,046, 17 pages.

USPTO Office Action dated Sep. 22, 2011 for U.S. Appl. No. 13/070,046, 15 pages.

USPTO Final Office Action dated Aug. 5, 2010 for U.S. Appl. No. 12/335,724, 10 pages.

USPTO Office Action dated Oct. 28, 2009 for U.S. Appl. No. 12/335,724, 18 pages.

USPTO Office Action dated Feb. 8, 2011 for U.S. Appl. No. 12/335,724, 8 pages.

USPTO Office Action dated Mar. 9, 2010 for U.S. Appl. No. 12/335,724, 7 pages.

USPTO Notice of Allowance dated Mar. 25, 2011 for U.S. Appl. No. 12/335,724, 5 pages.

USPTO Pre-Brief Appeal Conference Decision dated Dec. 1, 2010 for U.S. Appl. No. 12/335,724, 2 pages.

USPTO Office Action dated Aug. 20, 2010 for U.S. Appl. No. 12/390,965, 15 pages.

USPTO Notice of Allowance dated Nov. 3, 2010 for U.S. Appl. No. 12/390,965, 7 pages.

Safai, "Quantum Dot Detection", U.S. Appl. No. 13/226,750, filed Sep. 7, 2011, 45 pages.

Safai, "X-ray Inspection Tool", U.S. Appl. No. 12/952,652, filed Nov. 23, 2010, 38 pages.

Artemyev et al., "Quantum dots in photonic dots," Applied Physics Letters, vol. 96, Issue 11, Mar. 2000, pp. 1353-1355.

Bakkers et al., "Excited-State Dynamics in CdS Quantum Dots Absorbed on a Metal Electrode," Journal of Physical Chemistry, vol. 103, No. 14, Mar. 1999, pp. 2781-2788.

Bryant et al., "The use of fluorescent probes for the detection of under-film corrosion," Progress in Organic Coatings, vol. 57, Issue 4, Dec. 2006, pp. 416-420.

Hakim et al., "Nanocoating Individual Silica Nanoparticles by Atomic Layer Deposition in a Fluidized Bed Reactor," Chemical Vapor Deposition, vol. 11, Issue 10, Oct. 2005, pp. 420-425.

Yu et al., "Experimental determination of the extinction coefficient of CdTe, CdSe, and CdS nanocrystals," Chemistry of Materials, vol. 15, No. 14, Jun. 2003, pp. 2854-2860.

Shedlock et al., "X-Ray Backscatter Imaging for Aerospace Applications", 5 pages, retrieved Nov. 23, 2010.

X-RAY INSPECTION TOOL

BACKGROUND INFORMATION

1. Field

The present disclosure relates generally to X-ray systems and more specifically to a method and apparatus for inspecting a surface of a work piece.

2. Background

X-rays are frequently used to generate images of a surface of an object. X-rays are generated by an X-ray tube and directed at the surface. Some of the X-rays are reflected by the surface, while other X-rays are absorbed or penetrated through materials. X-rays that are reflected by the surface are referred to as backscattered X-rays. The X-rays that are backscattered are frequently reflected by metallic surfaces or inconsistencies in the surfaces. The X-rays that are absorbed are frequently absorbed by metallic and other suitable materials. The backscattered X-rays may be collected to generate an image of the surface.

X-rays may also be used to identify inconsistencies in a surface. For example, X-rays may be generated by an X-ray tube and directed at a metallic surface to identify inconsistencies in the metallic surface. One example of a metallic surface is the surface of a fuselage of an aircraft.

As the X-rays contact the metallic surface, an X-ray detector receives a portion of the X-rays that that are scattered back from the metallic surface to the X-ray detector. As used herein, scattering means reflecting. In other words, a portion of the X-rays is reflected back from the metallic surface to the X-ray detector. In the event that the X-rays contact an inconsistency in the metal surface, some of the X-rays may be allowed to pass through the surface and are not reflected back to the X-ray detector. Thus, the portion of the X-rays are not reflected back to the X-ray detector and the inconsistency is visible in the generated image.

In some examples, the surface may have a large surface area to inspect. To inspect the area using X-rays, the X-ray tube for generating the X-rays and the X-ray detector are moved over the surface area. The X-ray tube and X-ray detector may be part of a mechanism attached to a scaffolding and/or moved by a robotic arm. The scaffolding and/or robotic arm are repositioned to inspect areas of the surface that have a different curvature than the current area of inspection.

This positioning of the X-ray detector to inspect different areas of the surface increases as the surface area increases. With a large surface area, the time used to inspect the surface may be longer than desired.

Accordingly, it would be advantageous to have a method and apparatus which takes into account one or more of the issues discussed above, as well as possibly other issues.

SUMMARY

The different advantageous embodiments provide an apparatus and a method for inspecting a surface of a work piece. In one advantageous embodiment, an apparatus comprising a number of tracks, a support structure, an X-ray system, a connection system, and a controller is disclosed. The number of tracks are configured for placement along a path. The support structure is configured to move on the number of tracks. The X-ray system is moveably connected to the support structure, wherein the X-ray system is configured to send a plurality of X-rays toward a work piece and is configured to move along an axis through the support structure. The connection system is configured to removably connect the number of tracks to the work piece using a vacuum applied to a surface of the work piece. The controller is configured to activate and deactivate the X-ray system based on an amount of vacuum applied to the surface of the work piece.

The features, functions, and advantages can be achieved independently in various embodiments of the present disclosure or may be combined in yet other embodiments in which further details can be seen with reference to the following description and drawings.

BRIEF DESCRIPTION OF THE DRAWINGS

The novel features believed characteristic of the advantageous embodiments are set forth in the appended claims. The advantageous embodiments, however, as well as a preferred mode of use, further objectives and advantages thereof, will best be understood by reference to the following detailed description of an advantageous embodiment of the present disclosure when read in conjunction with the accompanying drawings, wherein:

DETAILED DESCRIPTION

Figure 1:
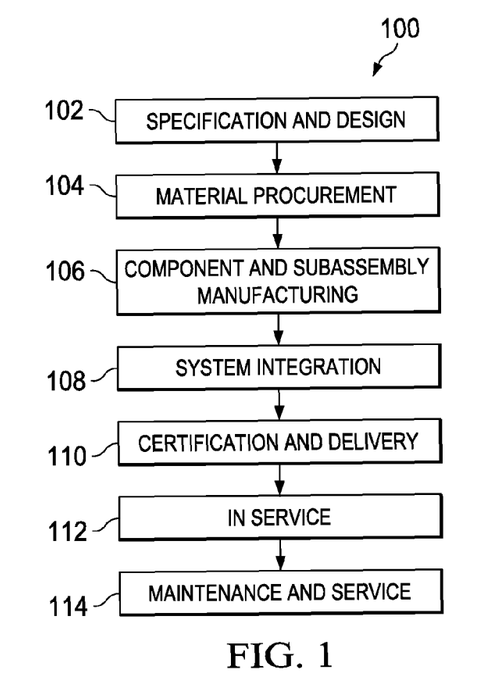
FIG. 1 is an illustration of an aircraft manufacturing and service method in accordance with an advantageous embodiment.
Figure 2:
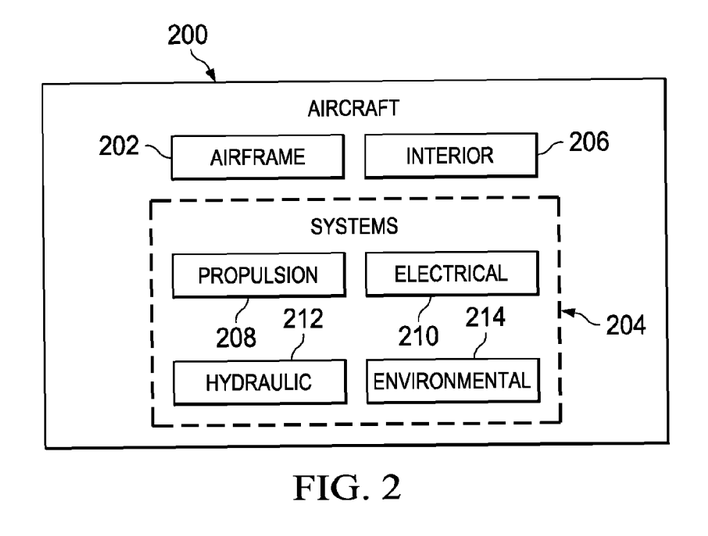
FIG. 2 is an illustration of an aircraft in which an advantageous embodiment may be implemented.

Referring more particularly to the drawings, embodiments of the disclosure may be described in the context of aircraft manufacturing and service method 100 as shown in FIG. 1 and aircraft 200 as shown in FIG. 2. Turning first to FIG. 1, an illustration of an aircraft manufacturing and service method is depicted in accordance with an advantageous embodiment. During pre-production, aircraft manufacturing and service method 100 may include specification and design 102 of aircraft 200 in FIG. 2 and material procurement 104.

During production, component and subassembly manufacturing 106 and system integration 108 of aircraft 200 in FIG. 2 takes place. Thereafter, aircraft 200 in FIG. 2 may go through certification and delivery 110 in order to be placed in service 112. While in service 112 by a customer, aircraft 200 in FIG. 2 is scheduled for routine maintenance and service 114, which may include modification, reconfiguration, refurbishment, and other maintenance or service.

The different advantageous embodiments may be used to inspect aircraft 200 in FIG. 2 during a number of different phases of aircraft manufacturing and service method 100. For example, the different advantageous embodiments may be used during certification and delivery 110 to identify inconsistencies in the aircraft prior to certification and delivery 110. In another example, the different advantageous embodiments may be used during in service 112 to identify inconsistencies that develop during operation of aircraft 200 in FIG. 2.

Each of the processes of aircraft manufacturing and service method 100 may be performed or carried out by a system integrator, a third party, and/or an operator. In these examples, the operator may be a customer. For the purposes of this description, a system integrator may include, without limitation, any number of aircraft manufacturers and major system subcontractors; a third party may include, without limitation, any number of vendors, subcontractors, and suppliers; and an operator may be an airline, leasing company, military entity, service organization, and so on.

With reference now to FIG. 2, an illustration of an aircraft is depicted in which an advantageous embodiment may be implemented. In this example, aircraft 200 is produced by aircraft manufacturing and service method 100 in FIG. 1 and may include airframe 202 with a plurality of systems 204 and interior 206. Examples of systems 204 include one or more of propulsion system 208, electrical system 210, hydraulic system 212, and environmental system 214. Any number of other systems may be included. Although an aerospace example is shown, the different advantageous embodiments may be applied to other industries, such as the automotive industry.

The different advantageous embodiments may be used to identify inconsistencies in a number of different areas of aircraft 200. For example, the different advantageous embodiments may be used to identify inconsistencies in airframe 202. Of course, other areas of aircraft may be inspected using the different advantageous embodiments.

Apparatus and methods embodied herein may be employed during at least one of the stages of aircraft manufacturing and service method 100 in FIG. 1. As used herein, the phrase "at least one of", when used with a list of items, means that different combinations of one or more of the listed items may be used and only one of each item in the list may be needed. For example, "at least one of item A, item B, and item C" may include, for example, without limitation, item A or item A and item B. This example also may include item A, item B, and item C or item B and item C.

In one illustrative example, components or subassemblies produced in component and subassembly manufacturing 106 in FIG. 1 may be fabricated or manufactured in a manner similar to components or subassemblies produced while aircraft 200 is in service 112 in FIG. 1. As yet another example, a number of apparatus embodiments, method embodiments, or a combination thereof may be utilized during production stages, such as component and subassembly manufacturing 106 and system integration 108 in FIG. 1. A number, when referring to items, means one or more items. For example, a number of apparatus embodiments is one or more apparatus embodiments. A number of apparatus embodiments, method embodiments, or a combination thereof may be utilized while aircraft 200 is in service 112 and/or during maintenance and service 114 in FIG. 1. The use of a number of the different advantageous embodiments may substantially expedite the assembly of and/or reduce the cost of aircraft 200.

The different advantageous embodiments recognize and take into account a number of different considerations. For example, the different advantageous embodiments recognize and take into account that repositioning an X-ray system using a robotic arm or a scaffolding is time-consuming. Additionally, labor costs increase with the size of the surface area to be inspected because the operator stops operation of the X-ray system, repositions the X-ray system, and resumes operation of the X-ray system. In these examples, the X-ray system is an X-ray backscattering system. In other words, the X-ray system is configured to receive X-rays that are reflected from the surface being tested.

The different advantageous embodiments also recognize and take into account that the X-ray system may be located on a number of tracks. The tracks may be extendable and form a path that contours to the shape of the surface to the inspected. The tracks may be temporarily connected to the surface of the work piece using suction cups and a vacuum system to remove the air from the suction cups that are connected to the work piece. The X-ray system moves on the tracks along the path. The X-ray system also moves between the tracks to provide two dimensional imaging data for the surface.

The different advantageous embodiments also recognize and take into account that forming the path with the number of tracks allows the X-ray system to move along the surface without being repositioned by an operator. Operator safety may be improved because the operator does not lift or move heavy equipment. Labor costs may also be reduced because the surface may be scanned without stopping operation of the X-ray system to reposition the X-ray system.

Thus, the different advantageous embodiments provide an apparatus and a method for inspecting a surface of a work piece. In one advantageous embodiment, an apparatus comprising a number of tracks, a support structure, an X-ray system, a connection system, and a controller is disclosed. The number of tracks is configured for placement along a path. The support structure is configured to move on the number of tracks. The X-ray system is moveably connected to the support structure, wherein the X-ray system is configured to send a plurality of X-rays toward a work piece and is configured to move along an axis through the support structure. The connection system is configured to removably connect the number of tracks to the work piece using a vacuum applied to a surface of the work piece. The controller is configured to activate and deactivate the X-ray system based on an amount of vacuum applied to the surface of the work piece. An example of the amount of vacuum is amount 352 of vacuum 346 in FIG. 3.

Figure 3:
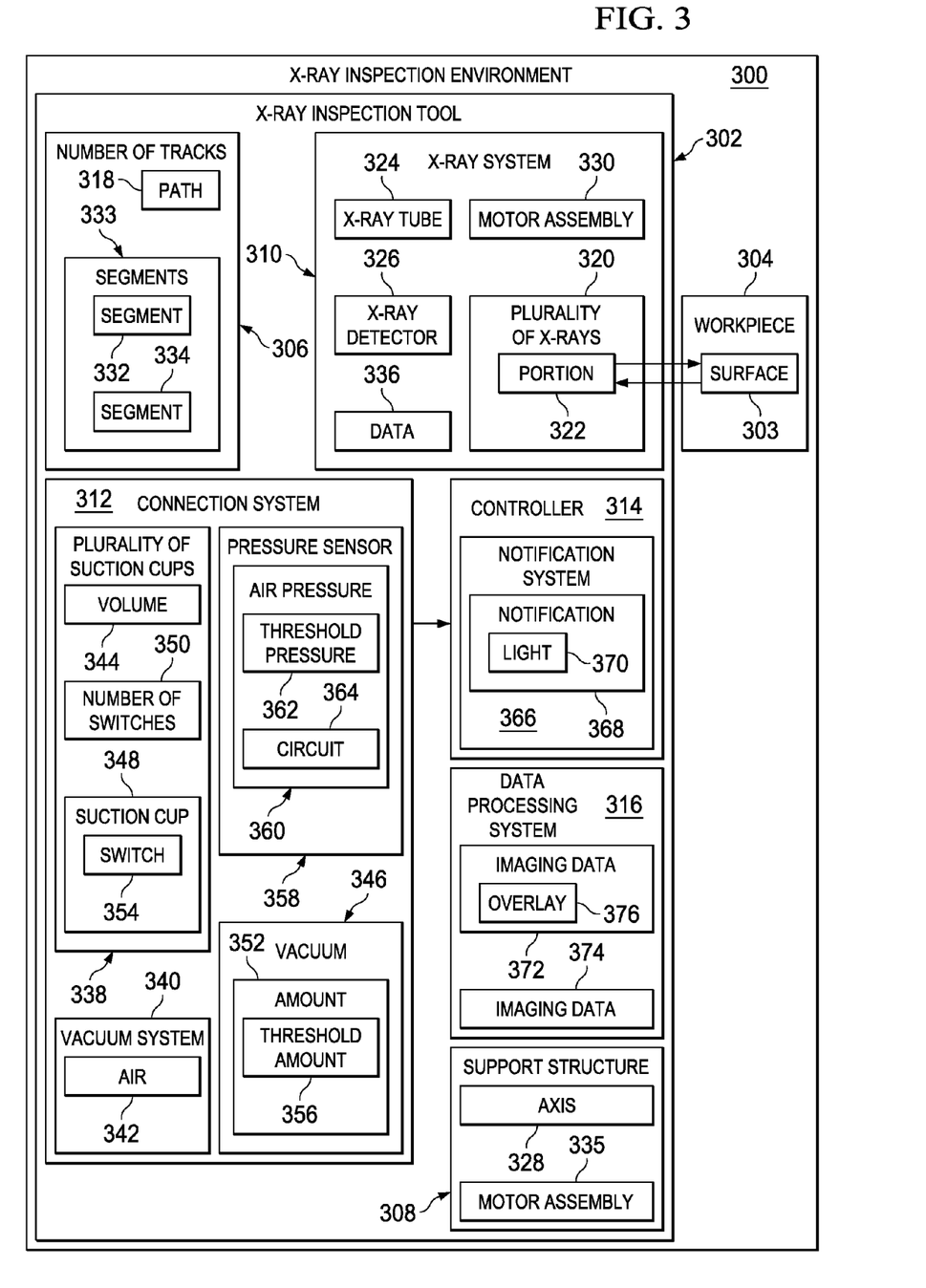
FIG. 3 is an illustration of a block diagram of an X-ray inspection environment in accordance with an advantageous embodiment.

Turning now to FIG. 3, an illustration of a block diagram of an X-ray inspection environment is depicted in accordance with an advantageous embodiment. X-ray inspection environment 300 is an example of an environment in which advantageous embodiments may be implemented.

In this advantageous embodiment, X-ray inspection environment 300 contains X-ray inspection tool 302 and work piece 304. X-ray inspection tool 302 inspects surface 303 of work piece 304 for inconsistencies in these examples.

X-ray inspection tool 302 includes number of tracks 306, support structure 308, X-ray system 310, connection system 312, controller 314, data processing system 316, and other suitable components. X-ray system 310 is a system that generates plurality of X-rays 320. In this advantageous embodiment, X-ray system 310 includes X-ray tube 324 and X-ray detector 326.

When X-ray inspection tool 302 is operating, X-ray system 310 generates plurality of X-rays 320 toward surface 303. X-ray system 310 then receives portion 322 of plurality of X-rays 320. Portion 322 is the X-rays in plurality of X-rays 320 that are reflected back toward X-ray system 310 from surface 303. In embodiments in which no X-rays in plurality of X-rays 320 are reflected back to X-ray system 310, portion 322 may be empty. X-ray inspection tool 302 is connected to support structure 308.

As used herein, when a first component is connected to a second component, the first component may be connected to the second component without any additional components. The first component also may be connected to the second component by one or more other components. For example, one electronic device may be connected to a second electronic device without any addition electronic devices between the first electronic device and the second electronic device. In some cases, another electronic device may be present between the two electronic devices connected to each other.

In this illustrative example, support structure 308 is a structure that extends along axis 328 and moves along number of tracks 306. In this advantageous embodiment, support structure 308 is a member. Of course, support structure 308 may also be a carriage or a member with a channel in which X-ray system 310 moves in other advantageous embodiments.

X-ray system 310 is moved along axis 328 of support structure 308 by motor assembly 330. Motor assembly 330 moves X-ray system 310 along axis 328 until X-ray system 310 reaches a track in number of tracks 306. In embodiments in which number of tracks 306 includes two tracks, motor assembly 330 moves X-ray system 310 between the two tracks along axis 328.

Motor assembly 330 moves X-ray system 310 to positions along axis 328. At each position, X-ray system 310 generates plurality of X-rays 320 and receives portion 322. X-ray system 310 generates data 336 for each position along axis 328 using portion 322.

In the depicted examples, data 336 includes the amount of X-rays contained in portion 322 and positional data for X-ray system 310. For example, data 336 may contain a value for the amount of X-rays and a set of coordinates for the position of X-ray system 310 along axis 328 and number of tracks 306. In one advantageous embodiment, the set of coordinates is represented as an (x,y) coordinate pair.

Number of tracks 306 is guides along which X-ray system 310 travels while generating plurality of X-rays 320. Number of tracks 306 is configured by an operator to form path 318. Each track in number of tracks 306 includes segments 333. For example, segment 332 of a track may form a straight line. On the other hand, segment 334 may form an arc. Segment 332 and segment 334 may be joined by an operator using a coupling within segment 332 and segment 334. Likewise, additional segments in segments 333 may be added. Once joined, the segments form a single track along which X-ray system 310 may travel.

In one advantageous embodiment, motor assembly 335 moves X-ray system 310 on number of tracks 306 along path 318. X-ray system 310 begins generating plurality of X-rays 320 at one end of number of tracks 306. Motor assembly 330 moves X-ray system 310 to positions along axis 328 on support structure 308. Data 336 is generated at each position.

Once X-ray system 310 has generated plurality of X-rays 320 for each position along axis 328, motor assembly 335 moves support structure 308 to another position along path 318. Thus, for each position along path 318 on number of tracks 306, X-ray system 310 generates data 336 for each position along axis 328.

In the illustrative examples, path 318 follows the shape of surface 303. For example, when surface 303 is a curved section of a fuselage, path 318 follows the shape of the curved section such that the distance between X-ray system 310 and surface 303 does not substantially change as X-ray system 310 moves on number of tracks 306 along path 318.

Number of tracks 306 are removably attached to work piece 304 using connection system 312. Connection system 312 includes plurality of suction cups 338 and vacuum system 340 in this advantageous embodiment. At least some components of connection system 312 may be associated with a side of each track in number of tracks 306 that contacts surface 303. For example, plurality of suction cups 338 may be associated with the side of number of tracks 306 that contacts surface 303.

A first component may considered to be associated with a second component by being secured to the second component, bonded to the second component, fastened to the second component, and/or connected to the second component in some other suitable manner. The first component also may be connected to the second component through using a third component. The first component may also be considered to be associated with the second component by being formed as part of and/or an extension of the second component.

An operator may position plurality of suction cups 338 such that plurality of suction cups 338 are in contact with surface 303. Plurality of suction cups 338 is a material shaped such that, once plurality of suction cups 338 are in contact with surface 303, air between plurality of suction cups 338 and surface 303 is inhibited from moving to the environment outside of plurality of suction cups 338.

The operator then activates vacuum system 340. Vacuum system 340 removes substantially all of air 342 from volume 344. Volume 344 is the region of space between plurality of suction cups 338 and surface 303. By removing substantially all of air 342 from volume 344, vacuum 346 is generated. Vacuum 346 is the absence of substantially all air in a volume of space.

Vacuum system 340 continues to generate vacuum 346 in volume 344 while X-ray system 310 is generating plurality of X-rays 320. In the event that suction cup 348 in plurality of suction cups 338 does not maintain a desired level of connection to work piece 304, X-ray system 310 is disabled to increase safety for the operator. In other words, operation of X-ray system 310 is changed to stop generating plurality of X-rays 320.

In one advantageous embodiment, plurality of suction cups 338 causes X-ray system 310 to stop generating plurality of X-rays 320 using number of switches 350. In such an advantageous embodiment, number of switches 350 is associated with the side of plurality of suction cups 338 that contacts surface 303 such that number of switches 350 is activated when amount 352 of vacuum 346 exceeds a predetermined amount.

For example, number of switches 350 may be activated when substantially all of air 342 is removed from volume 344. Thus, in the event that suction cup 348 does not maintain a desired level of connection to work piece 304, switch 354 in suction cup 348 becomes deactivated because pressure is no longer being applied to switch 354 by surface 303. In one advantageous embodiment, number of switches 350 are deactivated when amount 352 of vacuum 346 decreases below threshold amount 356.

When switch 354 becomes deactivated, a signal is sent to controller 314 that switch 354 has been deactivated. In these examples, number of switches 350 are connected to controller 314 in a series circuit such that when switch 354 is deactivated, the series circuit is opened. Thus, controller 314 may identify that the circuit is no longer closed and that X-ray system 310 is to be deactivated. Controller 314 deactivates X-ray system 310 by disengaging electric power to X-ray system 310 until suction cup 348 is reconnected or another action is taken by an operator. For example, the operator may flip a switch on controller 314 that causes controller 314 to reactivate X-ray system 310.

In other advantageous embodiments, number of switches 350 is absent. In such advantageous embodiments, pressure sensor 358 may be located in each of plurality of suction cups 338. When the operator activates X-ray system 310, air pressure 360 is continuously identified for volume 344 using pressure sensor 358. In the event that air pressure 360 decreases below threshold pressure 362, connection system 312 causes circuit 364 to be opened. In other words, air pressure 360 may decrease below threshold pressure 362 such that the desired level of connection to surface 303 is not maintained. Thus, controller 314 identifies that circuit 364 is open and deactivates X-ray system 310 by disengaging electric power to X-ray system 310.

Controller 314 also includes notification system 366. Notification system 366 generates notification 368 for a human operator that X-ray system 310 is generating plurality of X-rays 320. In this advantageous embodiment, notification 368 includes light 370. Of course, in other advantageous embodiments, notification 368 may consist of an audio alert, a vibration alert, a visual message, or another suitable notification.

Once X-ray system 310 has generated data 336, data 336 is sent to data processing system 316. Data 336 may be sent over a wired connection or a wireless connection. Data processing system 316 receives data 336. In the depicted examples, data 336 includes the positional data for X-ray system 310, the amount of portion 322 received by X-ray system 310 at the position, and other suitable type of data.

Data processing system 316 generates imaging data 372 using data 336. Imaging data 372 is a two-dimensional digital image of surface 303 as seen in X-ray light. An example of imaging data 372 is depicted in screenshot 800 in FIG. 8.

Figure 4:
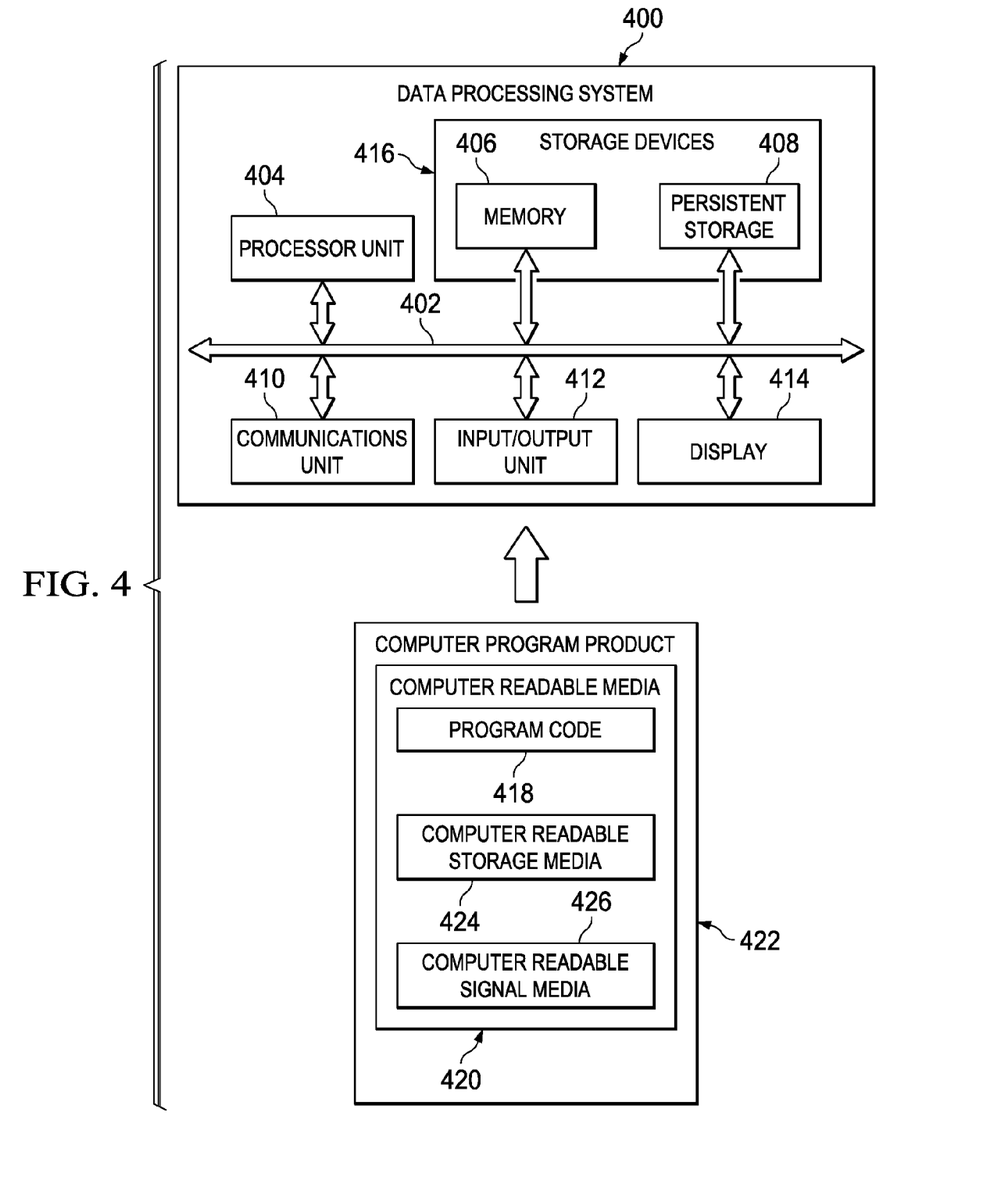
FIG. 4 is an illustration of a data processing system in accordance with an advantageous embodiment.

Data processing system 316 presents imaging data 372 using a display, such as display 414 in FIG. 4. Data processing system 316 may also present imaging data 374 with imaging data 372. Imaging data 374 is a digital image of work piece 304 as seen in visible light. Imaging data 374 may be generated by a digital imaging system used by an operator. Of course, imaging data 374 may also be generated by a digital imaging system component of X-ray inspection tool 302.

In one advantageous embodiment, imaging data 372 is presented simultaneously with imaging data 374 but in different locations on the display. In other advantageous embodiments, data processing system 316 presents overlay 376. Overlay 376 is a presentation in which imaging data 372 is presented translucently over imaging data 374 such that the position and size of work piece 304 is the same in both imaging data 372 and imaging data 374. Thus, an operator may view the visible light imagery and the X-ray imagery of the same location on work piece 304.

The illustration of X-ray inspection tool 302 in X-ray inspection environment 300 in FIG. 3 is not meant to imply physical or architectural limitations to the manner in which different features may be implemented. Other components in addition to and/or in place of the ones illustrated may be used. Some components may be unnecessary in some advantageous embodiments. Also, the blocks are presented to illustrate some functional components. One or more of these blocks may be combined and/or divided into different blocks when implemented in different advantageous embodiments.

For example, in some advantageous embodiments, number of tracks 306 includes a single track. In such an advantageous embodiment, motor assembly 330 may be absent and X-ray system 310 may not travel along axis 328. Instead, X-ray system 310 may generate data 336 only for positions on number of tracks 306 along path 318.

In some other advantageous embodiments, plurality of suction cups 338 contains both number of switches 350 and pressure sensor 358. In such an advantageous embodiment, circuit 364 may be opened by either air pressure 360 decreasing below threshold pressure 362 or amount 352 of vacuum 346 decreasing below threshold amount 356.

Additionally, data processing system 316 may be implemented as circuits or a programmable logic array instead of a data processing system. In other advantageous embodiments, controller 314 is a hardware and/or software component of data processing system 316.

Turning now to FIG. 4, an illustration of a data processing system is depicted in accordance with an advantageous embodiment. Data processing system 400 is an example implementation of data processing system 316 in FIG. 3. In this illustrative example, data processing system 400 includes communications fabric 402, which provides communications between processor unit 404, memory 406, persistent storage 408, communications unit 410, input/output (I/O) unit 412, and display 414.

Processor unit 404 serves to execute instructions for software that may be loaded into memory 406. Processor unit 404 may be a number of processors, a multi-processor core, or some other type of processor, depending on the particular implementation. A number, as used herein with reference to an item, means one or more items. Further, processor unit 404 may be implemented using a number of heterogeneous processor systems in which a main processor is present with secondary processors on a single chip. As another illustrative example, processor unit 404 may be a symmetric multi-processor system containing multiple processors of the same type.

Memory 406 and persistent storage 408 are examples of storage devices 416. A storage device is any piece of hardware that is capable of storing information, such as, for example, without limitation, data, program code in functional form, and/or other suitable information either on a temporary basis and/or a permanent basis. Storage devices 416 may also be referred to as computer readable storage devices in these examples. Memory 406, in these examples, may be, for example, a random access memory or any other suitable volatile or non-volatile storage device. Persistent storage 408 may take various forms, depending on the particular implementation.

For example, persistent storage 408 may contain one or more components or devices. For example, persistent storage 408 may be a hard drive, a flash memory, a rewritable optical disk, a rewritable magnetic tape, or some combination of the above. The media used by persistent storage 408 also may be removable. For example, a removable hard drive may be used for persistent storage 408.

Communications unit 410, in these examples, provides for communications with other data processing systems or devices. In these examples, communications unit 410 is a network interface card. Communications unit 410 may provide communications through the use of either or both physical and wireless communications links.

Input/output unit 412 allows for input and output of data with other devices that may be connected to data processing system 400. For example, input/output unit 412 may provide a connection for user input through a keyboard, a mouse, and/or some other suitable input device. Further, input/output unit 412 may send output to a printer. Display 414 provides a mechanism to display information to a user.

Instructions for the operating system, applications, and/or programs may be located in storage devices 416, which are in communication with processor unit 404 through communications fabric 402. In these illustrative examples, the instructions are in a functional form on persistent storage 408. These instructions may be loaded into memory 406 for execution by processor unit 404. The processes of the different embodiments may be performed by processor unit 404 using computer implemented instructions, which may be located in a memory, such as memory 406.

These instructions are referred to as program code, computer usable program code, or computer readable program code that may be read and executed by a processor in processor unit 404. The program code in the different embodiments may be embodied on different physical or computer readable storage media, such as memory 406 or persistent storage 408.

Program code 418 is located in a functional form on computer readable media 420 that is selectively removable and may be loaded onto or transferred to data processing system 400 for execution by processor unit 404. Program code 418 and computer readable media 420 form computer program product 422 in these examples. In one example, computer readable media 420 may be computer readable storage media 424 or computer readable signal media 426. Computer readable storage media 424 may include, for example, an optical or magnetic disk that is inserted or placed into a drive or other device that is part of persistent storage 408 for transfer onto a storage device, such as a hard drive, that is part of persistent storage 408. Computer readable storage media 424 also may take the form of a persistent storage, such as a hard drive, a thumb drive, or a flash memory, that is connected to data processing system 400. In some instances, computer readable storage media 424 may not be removable from data processing system 400. In these illustrative examples, computer readable storage media 424 is a non-transitory computer readable storage medium.

Alternatively, program code 418 may be transferred to data processing system 400 using computer readable signal media 426. Computer readable signal media 426 may be, for example, a propagated data signal containing program code 418. For example, computer readable signal media 426 may be an electromagnetic signal, an optical signal, and/or any other suitable type of signal. These signals may be transmitted over communications links, such as wireless communications links, optical fiber cable, coaxial cable, a wire, and/or any other suitable type of communications link. In other words, the communications link and/or the connection may be physical or wireless in the illustrative examples.

In some advantageous embodiments, program code 418 may be downloaded over a network to persistent storage 408 from another device or data processing system through computer readable signal media 426 for use within data processing system 400. For instance, program code stored in a computer readable storage medium in a server data processing system may be downloaded over a network from the server to data processing system 400. The data processing system providing program code 418 may be a server computer, a client computer, or some other device capable of storing and transmitting program code 418.

The different components illustrated for data processing system 400 are not meant to provide architectural limitations to the manner in which different embodiments may be implemented. The different advantageous embodiments may be implemented in a data processing system, including components in addition to or in place of those illustrated for data processing system 400. Other components shown in FIG. 4 can be varied from the illustrative examples shown. The different embodiments may be implemented using any hardware device or system capable of running program code. As one example, the data processing system may include organic components integrated with inorganic components and/or may be comprised entirely of organic components excluding a human being. For example, a storage device may be comprised of an organic semiconductor.

In another illustrative example, processor unit 404 may take the form of a hardware unit that has circuits that are manufactured or configured for a particular use. This type of hardware may perform operations without needing program code to be loaded into a memory from a storage device to be configured to perform the operations.

For example, when processor unit 404 takes the form of a hardware unit, processor unit 404 may be a circuit system, an application specific integrated circuit (ASIC), a programmable logic device, or some other suitable type of hardware configured to perform a number of operations. With a programmable logic device, the device is configured to perform the number of operations. The device may be reconfigured at a later time or may be permanently configured to perform the number of operations. Examples of programmable logic devices include, for example, a programmable logic array, a programmable array logic, a field programmable logic array, a field programmable gate array, and other suitable hardware devices. With this type of implementation, program code 418 may be omitted because the processes for the different embodiments are implemented in a hardware unit.

In still another illustrative example, processor unit 404 may be implemented using a combination of processors found in computers and hardware units. Processor unit 404 may have a number of hardware units and a number of processors that are configured to run program code 418. With this depicted example, some of the processes may be implemented in the number of hardware units, while other processes may be implemented in the number of processors.

As another example, a storage device in data processing system 400 is any hardware apparatus that may store data. Memory 406, persistent storage 408, and computer readable media 420 are examples of storage devices in a tangible form.

In another example, a bus system may be used to implement communications fabric 402 and may be comprised of one or more buses, such as a system bus or an input/output bus. Of course, the bus system may be implemented using any suitable type of architecture that provides for a transfer of data between different components or devices attached to the bus system. Additionally, a communications unit may include one or more devices used to transmit and receive data, such as a modem or a network adapter. Further, a memory may be, for example, memory 406, or a cache, such as found in an interface and memory controller hub that may be present in communications fabric 402.

Data processing system 400 may be used in the different advantageous embodiments to receive and store data from an X-ray system. For example, data processing system 400 may receive the data using communications unit third user 410. Data processing system 400 may then store the data using any of storage devices 416. The data received from the X-ray system may be data used to generate imaging data of the surface. For example, the data received may consist of amount of X-rays received and/or positional data for the X-ray system.

Figure 5:
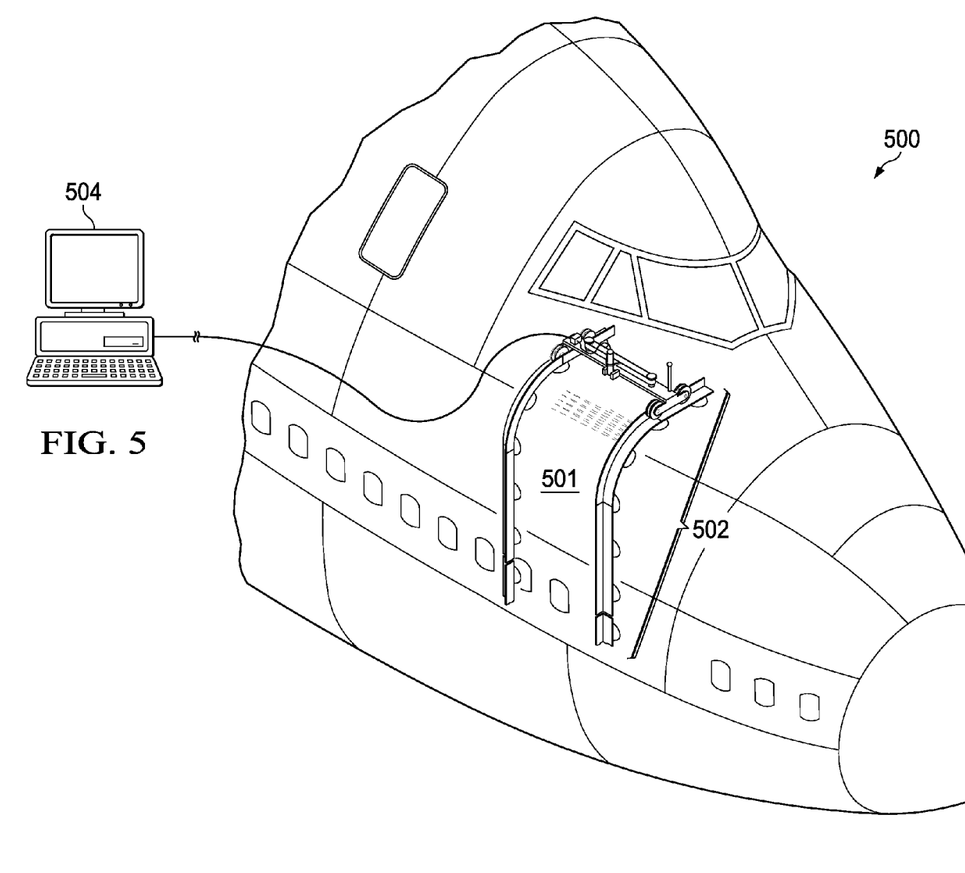
FIG. 5 is an illustration of an aircraft in accordance with an advantageous embodiment.

Looking now to FIG. 5, an illustration of an aircraft is depicted in accordance with advantageous embodiments. Aircraft 500 is an example of one implementation of aircraft 200 in FIG. 2.

In this illustrative example, aircraft 500 is being inspected for inconsistencies. More specifically, section 501 of aircraft 500 is being inspected for inconsistencies using X-ray inspection tool 502. X-ray inspection tool 502 is an example of one implementation of X-ray inspection tool 302 in FIG. 3.

Data processing system 504 is an example implementation of data processing system 316. Data processing system 504 receives data from X-ray inspection tool 502 and generates imaging data using the data received from X-ray inspection tool 502.

Figure 6:
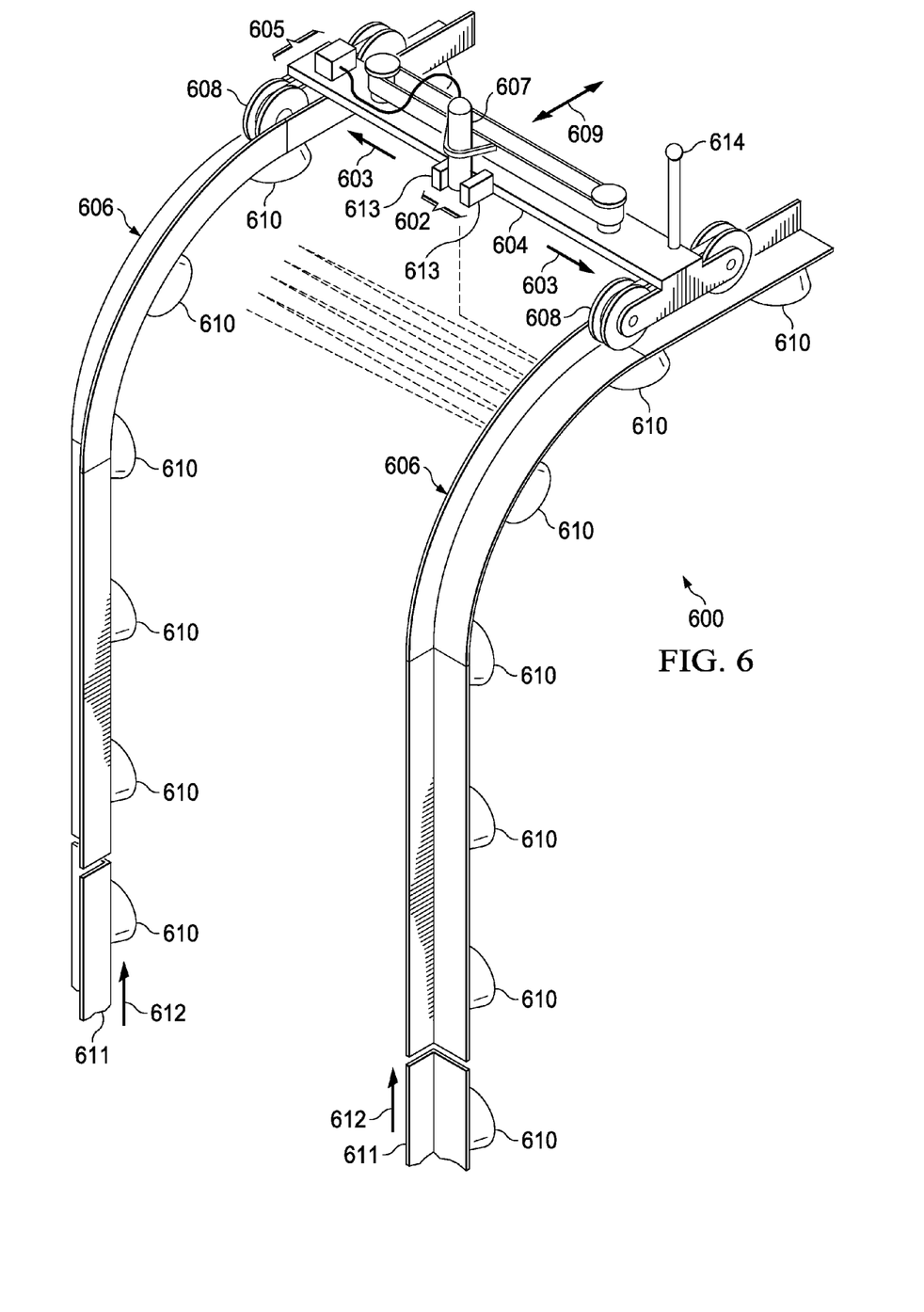
FIG. 6 is an illustration of an X-ray inspection tool in accordance with an advantageous embodiment.

Turning now to FIG. 6, an illustration of an X-ray inspection tool is depicted in accordance with an advantageous embodiment. X-ray inspection tool 600 is an enlarged view of X-ray inspection tool 502 in FIG. 5.

X-ray inspection tool 600 contains X-ray system 602. X-ray system 602 is an example implementation of X-ray system 310 in FIG. 3. In these examples, the X-ray system is an X-ray backscattering system. Of course, in other illustrative examples, other suitable types of X-ray systems may be used. In this advantageous embodiment, X-ray system 602 includes X-ray tube 607 and X-ray detectors 613. In these examples, X-ray detectors 613 are solid state detectors. However, in other illustrative examples, X-ray detectors 613 may be photomultiplier detectors or other suitable types of detectors.

X-ray system 602 is supported by support system 604. Support system 604 is a member in this advantageous embodiment. X-ray system 602 is moved along support system 604 in directions 603 by motor assembly 605. Motor assembly 605 is an example implementation of motor assembly 330 in FIG. 3. In this advantageous embodiment, motor assembly 605 includes a belt to which X-ray system 602 is attached, and a motor that moves the belt in directions 603.

Support system 604 also includes driven wheels 608 in this advantageous embodiment. Driven wheels 608 are a component in a motor assembly, such as motor assembly 335 in FIG. 3. Driven wheels 608 move X-ray inspection tool 600 along tracks 606 in directions 609.

Tracks 606 are an example implementation of number of tracks 306 in FIG. 3. Tracks 606 consist of multiple segments. In this advantageous embodiment, segments 611 are being added to tracks 606. Segments 611 consist of a mechanism such that when segments 611 are moved in direction 612 toward tracks 606, segments 611 become associated with tracks 606.

Connection system 610 is an example implementation of connection system 312 in FIG. 3. In this advantageous embodiment, connection system 610 includes suction cups. Connection system 610 removably attaches to a work piece, such as section 501 of aircraft 500 in FIG. 5.

Light 614 is an example implementation of light 370 in FIG. 3. Light 614 is illuminated when X-ray system 602 is generating X-rays in the depicted examples. Light 614 is an indicator for an operator or other human that X-ray system 602 is in use. Of course, other indicators may be present in other advantageous embodiments. For example, an audio alert may be present.

Figure 7:
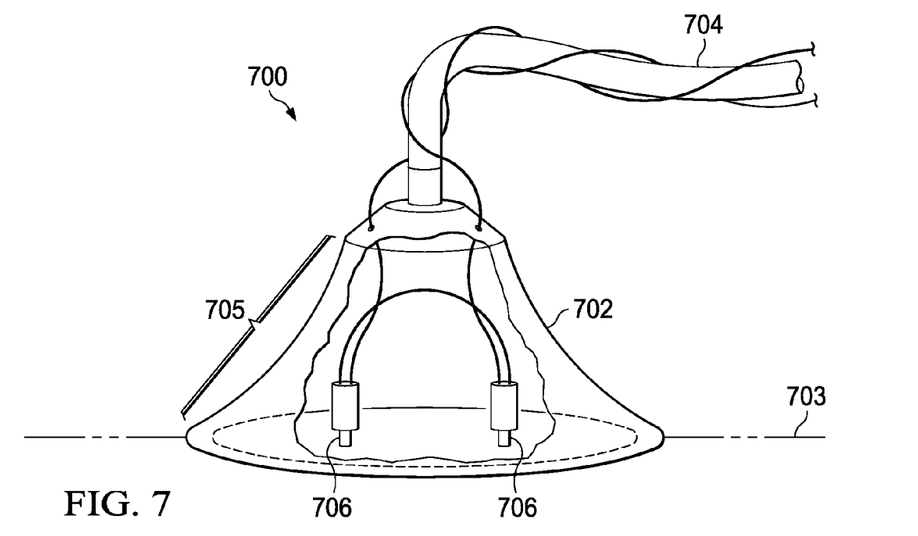
FIG. 7 is an illustration of a connection system in accordance with an advantageous embodiment.

Turning now to FIG. 7, an illustration of a connection system is depicted in accordance with an advantageous embodiment. Connection system 700 is an example implementation of connection system 312 in FIG. 3.

Suction cup 702 connects tracks, such as tracks 606 in FIG. 6, to surface 703. Suction cup 702 is shaped such that movement of air into volume 705 from outside of volume 705 is reduced. Volume 705 is an example implementation of volume 344 in FIG. 3.

To connect suction cup 702 to surface 703, a vacuum system is activated. The vacuum system removes air from volume 705 through vacuum line 704. As air is removed from volume 705, the increase in air pressure inside volume 705 causes suction cup 702 to compress toward surface 703 such that switches 706 are activated.

Once switches 706 are activated, an X-ray system may be activated by a controller. In the event that suction cup 702 becomes disconnected or loose from surface 703, switches 706 become deactivated because the air pressure in volume 705 decreases. Once switches 706 are deactivated, the controller may switch off power to the X-ray system.

Figure 8:
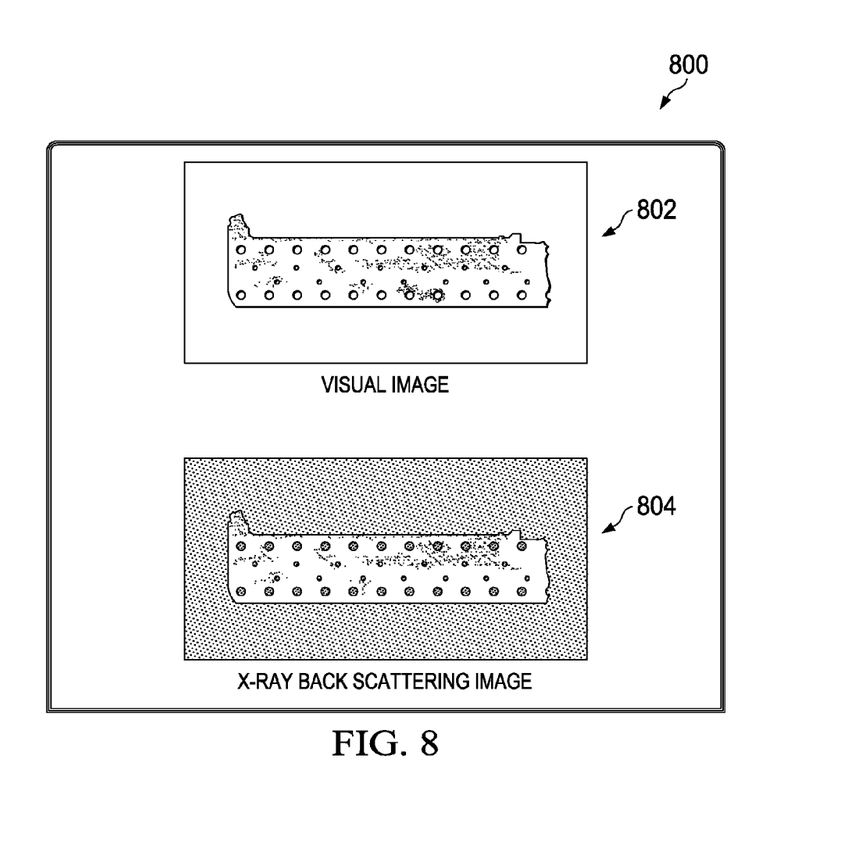
FIG. 8 is an illustration of a screenshot of imaging data in accordance with an advantageous embodiment.

Looking now to FIG. 8, an illustration of a screenshot of imaging data is presented in accordance with an advantageous embodiment. Screenshot 800 may be generated by a data processing system, such as data processing system 316 in FIG. 3 and presented on a display, such as display 414 in FIG. 4.

Screenshot 800 presents imaging data 802 and imaging data 804. Imaging data 802 shows a visible light digital image of a work piece. Imaging data 804 shows an X-ray digital image of the same work piece. Thus, an operator may inspect the two images simultaneously. Likewise, imaging data 802 and imaging data 804 may be presented as an overlay. In other words, imaging data 804 may be presented translucently over imaging data 802 such that the position, size, and location of the work piece are substantially the same in imaging data 802 and imaging data 804.

Figure 9:
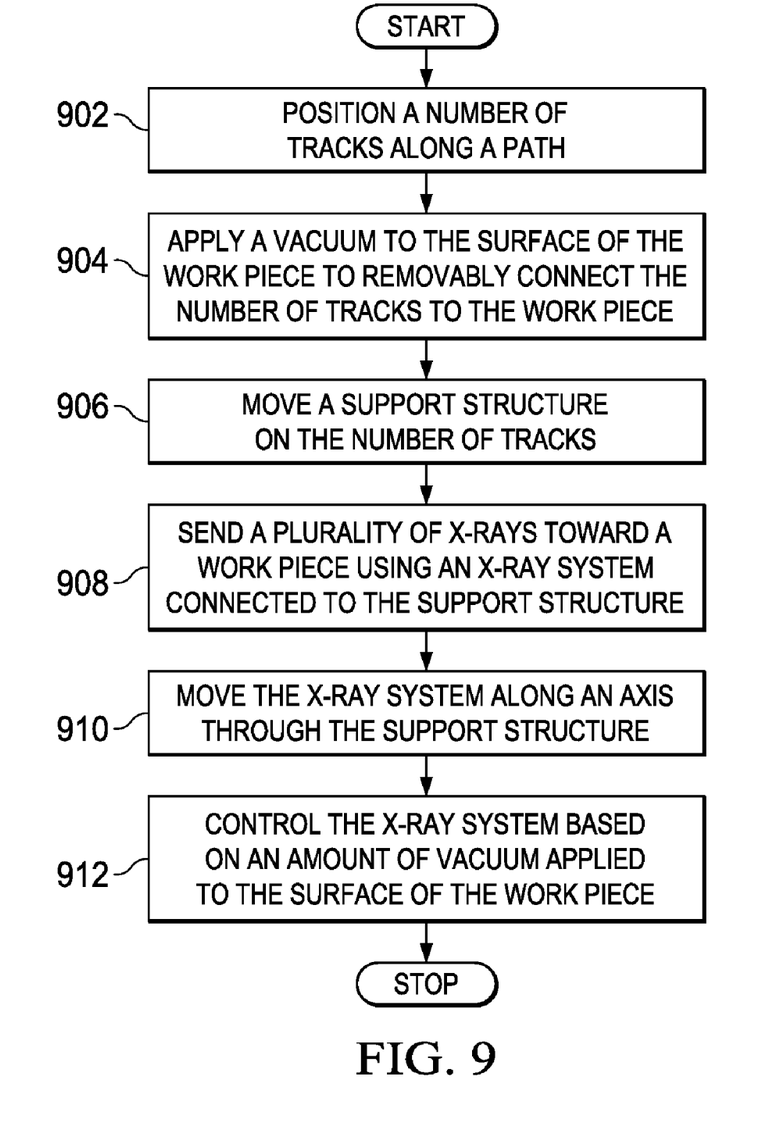
FIG. 9 is an illustration of a flowchart of a process for inspecting a surface of a work piece in accordance with an advantageous embodiment.

Looking now to FIG. 9, an illustration of a flowchart of a process for inspecting a surface of a work piece is depicted in accordance with an advantageous embodiment. The process may be performed by X-ray inspection tool 302 in X-ray inspection environment 300.

The process begins by positioning a number of tracks along a path (operation 902). The number of tracks may be number of tracks 306 and the path may be path 318 in X-ray inspection tool 302 in FIG. 3. Next, the process applies a vacuum to the surface of the work piece to removably connect the number of tracks to the work piece (operation 904). The vacuum may be vacuum 346 in connection system 312 in FIG. 3. The vacuum may be applied such that substantially no air is present in the area between the plurality of suction cups and the surface of the work piece. The vacuum inhibits movement of the plurality of suction cups away from or along the surface.

The process then moves a support structure on the number of tracks (operation 906). The support structure may be support structure 308 in X-ray inspection tool 302 in FIG. 3. In one advantageous embodiment, the support structure is a member moved along the number of tracks by a motor assembly. The motor assembly may consist of wheels that travel along the number of tracks.

Next, the process sends a plurality of X-rays toward a work piece using an X-ray system connected to the support structure (operation 908). The work piece may be work piece 304 in X-ray inspection environment 300, the plurality of X-rays may be plurality of X-rays 320 in X-ray system 310, and the X-ray system may be X-ray system 310 in X-ray inspection tool 302 in FIG. 3. In these examples, the X-ray system is an X-ray backscattering system. Of course, in other illustrative examples, other suitable types of X-ray systems may be used. A portion of the plurality of X-rays is received by an X-ray detector in the X-ray system. The portion of the plurality of X-rays includes the X-rays that are reflected back from the work piece.

The process then moves the X-ray system along an axis through the support structure (operation 910). The axis may be axis 328 of support structure 308 in FIG. 3.

Finally, the process controls the X-ray system based on an amount of vacuum applied to the surface of the work piece (operation 912). The amount of vacuum may be amount 352 in vacuum 346 in connection system 312 in FIG. 3. In one advantageous embodiment, the X-ray system is disengaged when the amount of vacuum decreases below a threshold amount of vacuum. A number of switches, a pressure sensor, or another suitable device may identify when the amount of vacuum has decreased below the threshold amount of vacuum. The process terminates thereafter.

Figure 10:
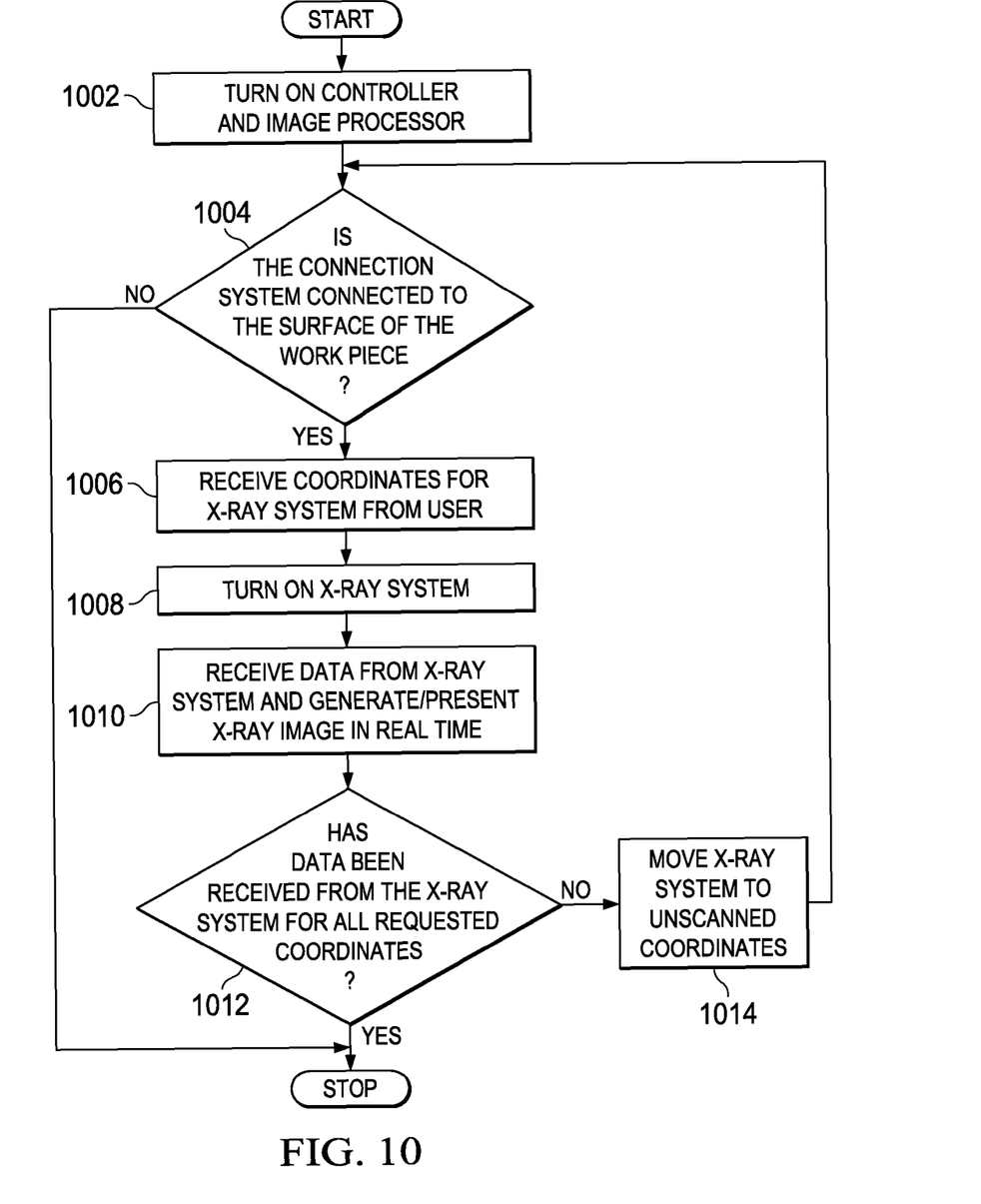
FIG. 10 is a further illustration of a flowchart of a process for inspecting a surface of a work piece in accordance with an advantageous embodiment.

Turning now to FIG. 10, a further illustration of a flowchart of a process for inspecting a surface of a work piece is depicted in accordance with an advantageous embodiment. The process may be performed by X-ray inspection tool 302 in X-ray inspection environment 300.

The process begins by turning on the controller and image processor (operation 1002). The image processor may be a data processing system in some advantageous embodiments. The process then determines whether the connection system is connected to the surface of the work piece (operation 1004). If the process determines that the connection system is not connected to the surface of the work piece, the process terminates. The process may perform operation 1004 by identifying whether a circuit for the connection system is closed or open.

If the processor determines that the connection system is connected to the surface of the work piece at operation 1004, the process receives coordinates for the X-ray system from the user (operation 1006). The coordinates may be a series or range of (x,y) coordinates. The process then turns on the X-ray system (operation 1008). In these examples, the X-ray system is an X-ray backscattering system. Of course, in other illustrative examples, other suitable types of X-ray systems may be used. The process then receives data from the X-ray system, generates the X-ray image in real time, and presents the X-ray image in real time (operation 1010).

The process then determines whether data has been received from the X-ray system for all requested coordinates (operation 1012). If the process determines that data has been received for all requested coordinates, the process terminates. If the process determines that data has not been received for all requested coordinates at operation 1012, the process moves the X-ray system to unscanned coordinates (operation 1014). The process then returns to operation 1004.

The flowcharts and block diagrams in the different depicted embodiments illustrate the architecture, functionality, and operation of some possible implementations of apparatus, methods and computer program products. In this regard, each block in the flowchart or block diagrams may represent a module, segment, or portion of computer usable or readable program code, which comprises one or more executable instructions for implementing the specified function or functions. In some alternative implementations, the function or functions noted in the block may occur out of the order noted in the figures. For example, in some cases, two blocks shown in succession may be executed substantially concurrently, or the blocks may sometimes be executed in the reverse order, depending upon the functionality involved.

For example, the process may not perform operation 1006 in the event that the process has already received the coordinates from the user and has moved the X-ray system to unscanned coordinates at operation 1014. Additionally, in an advantageous embodiment in which a visible light digital camera is also present, the process may also generate visible light imaging data at operation 1008.

Thus, the different advantageous embodiments provide increased safety for operators and reduced labor costs while performing X-ray inspection on a work piece. Safety is increased because the X-ray system disengages if the system becomes detached from the surface of the work piece. Additionally, labor costs are reduced because the operator does not need to disable the X-ray system for a period of time while the operator repositions the X-ray system.

Thus, the different advantageous embodiments provide an apparatus and a method for inspecting a surface of a work piece. In one advantageous embodiment, an apparatus comprising a number of tracks, a support structure, an X-ray system, a connection system, and a controller is disclosed. The number of tracks are configured for placement along a path. The support structure is configured to move on the number of tracks. The X-ray system is moveably connected to the support structure, wherein the X-ray system is configured to send a plurality of X-rays toward a work piece and is configured to move along an axis through the support structure. The connection system is configured to removably connect the number of tracks to the work piece using a vacuum applied to a surface of the work piece. The controller is configured to control the X-ray system based on an amount of vacuum applied to the surface of the work piece.

The description of the different advantageous embodiments has been presented for purposes of illustration and description, and is not intended to be exhaustive or limited to the embodiments in the form disclosed. Many modifications and variations will be apparent to those of ordinary skill in the art. Further, different advantageous embodiments may provide different advantages as compared to other advantageous embodiments. The embodiment or embodiments selected are chosen and described in order to best explain the principles of the embodiments, the practical application, and to enable others of ordinary skill in the art to understand the disclosure for various embodiments with various modifications as are suited to the particular use contemplated.

What is claimed is:

1. An apparatus comprising:
   a number of tracks configured for placement along a path;
   a support structure configured to move on the number of tracks;
   an X-ray system moveably connected to the support structure, wherein the X-ray system is configured to send a plurality of X-rays toward a work piece and is configured to move along an axis through the support structure;
   a connection system configured to removably connect the number of tracks to the work piece using a vacuum applied to a surface of the work piece; and
   a controller configured to activate and deactivate the X-ray system based on an amount of vacuum applied to the surface of the work piece.

2. The apparatus of claim 1, wherein the connection system comprises:
   a plurality of suction cups configured to removably connect the number of tracks to the work piece; and
   a vacuum system configured to remove air from a volume bound by each of the plurality of suction cups and the work piece.

3. The apparatus of claim 2, wherein each of the plurality of suction cups comprises:
   a number of switches located in the volume and configured to activate when substantially all of the air is removed from the volume.

4. The apparatus of claim 2, wherein each of the plurality of suction cups comprises:
   a pressure sensor configured to open a circuit when an air pressure in the volume increases above a threshold pressure.

5. The apparatus of claim 2, wherein the controller being configured to activate and deactivate the X-ray system based on the amount of vacuum applied to the surface of the work piece comprises the controller being configured to cause the X-ray system to cease generating the plurality of X-rays when the amount of vacuum decreases below a threshold amount of vacuum.

6. The apparatus of claim 1, wherein the support structure comprises:
   a motor assembly configured to move the X-ray system along the support structure.

7. The apparatus of claim 6, wherein the motor assembly is a first motor assembly, and further comprising:
   a second motor assembly configured to move the support structure on the number of tracks along the path.

8. The apparatus of claim 1 further comprising:
   a data processing system, wherein the data processing system is configured to receive data generated by the X-ray system.

9. The apparatus of claim 8, wherein the data processing system is further configured to generate imaging data for the work piece using the data.

10. The apparatus of claim 1 further comprising:
    a notification system configured to generate a light when the X-ray system is generating the plurality of X-rays.

11. An apparatus comprising:
    a number of tracks configured for placement along a surface of a work piece;
    a support structure configured to move on the number of tracks;
    an X-ray system moveably connected to the support structure, wherein the X-ray system is configured to send a plurality of X-rays toward the work piece and receive a portion of the plurality of X-rays reflected from the surface of the work piece;
    a motor assembly configured to move the X-ray system along the support structure;
    a connection system configured to removably connect the number of tracks to the surface of the work piece; and
    a data processing system configured to activate and deactivate the X-ray system based on an amount of vacuum applied to the surface of the work piece, to receive data from the X-ray system using the portion of the plurality of X-rays received by the X-ray system, and to generate imaging data using the data.

12. The apparatus of claim 11, wherein the data processing system is further configured to store the imaging data.

13. The apparatus of claim 11, wherein the imaging data is a first imaging data, and wherein the data processing system is further configured to present an overlay including the first imaging data and a second imaging data of the surface of the work piece.

14. A method for inspecting a surface of a work piece comprising:
    positioning a number of tracks along a path;
    applying a vacuum to the surface of the work piece to removably connect the number of tracks to the work piece;
    moving a support structure on the number of tracks;
    sending a plurality of X-rays toward the work piece using an X-ray system connected to the support structure;
    moving the X-ray system along an axis through the support structure; and
    activating and deactivating the X-ray system based on an amount of vacuum applied to the surface of the work piece.

15. The method of claim 14, wherein the step of applying the vacuum to the surface of the work piece to removably connect the number of tracks to the work piece comprises:
    removing air from a volume bound by each of a plurality of suction cups and the work piece.

16. The method of claim 15, wherein the step of applying the vacuum to the surface of the work piece to removably connect the number of tracks to the work piece further comprises:
    activating, by the surface of the work piece, a number of switches located in the volume when substantially all of the air is removed from the volume.

17. The method of claim 15, wherein the step of applying the vacuum to the surface of the work piece to removably connect the number of tracks to the work piece further comprises:
    determining whether an air pressure in the volume is above a threshold pressure; and
    responsive to a determination that the air pressure in the volume is above the threshold pressure, opening a circuit.

18. The method of claim 14 further comprising:
    moving the X-ray system along the support structure using a motor assembly.

19. The method of claim 14 further comprising:
    generating a notification when the X-ray system is generating the plurality of X-rays.

20. The method of claim 14 further comprising:
    generating first imaging data for the X-ray system using data received from the X-ray system; and
    presenting an overlay including the first imaging data of the surface of the work piece and second imaging data of the surface of the work piece, wherein the second imaging data is generated using visible light.

* * * * *